United States Patent [19]

Spring et al.

[11] Patent Number: 5,643,721
[45] Date of Patent: Jul. 1, 1997

[54] BIOREAGENT IMMOBILIZATION MEDIUM

[75] Inventors: Thomas G. Spring, Highland Park, Ill.; John M. Brackett, Kenosha, Wis.; Sheila A. Vogdes, Grayslake; Steven G. Schultz, Winthrop Harbor, both of Ill.

[73] Assignee: Abbott Laboratories, Abbott Park, Ill.

[21] Appl. No.: 193,972

[22] Filed: Feb. 9, 1994

[51] Int. Cl.$^6$ ............... G01N 33/543; G01N 33/545; G01N 33/548; G01N 33/551
[52] U.S. Cl. ............... 435/6; 204/400; 204/403; 204/409; 204/290 R; 252/500; 252/502; 252/503; 252/504; 252/506; 252/507; 252/508; 252/510; 252/511; 252/514; 252/516; 252/518; 422/82.01; 435/178; 435/179; 435/180; 435/817; 436/518; 436/524; 436/528; 436/806
[58] Field of Search ............... 252/500, 502, 252/503, 504, 506, 507, 508, 510, 511, 514, 516, 518, 520; 204/400, 703, 409, 290 R; 435/174, 177, 176, 178, 179, 180, 817, 25, 6; 436/518, 524, 525, 527, 528, 529, 531, 533, 534, 806, 535; 422/82.01

[56] References Cited

U.S. PATENT DOCUMENTS

| | | | |
|---|---|---|---|
| 3,519,538 | 7/1970 | Messing et al. | 195/63 |
| 4,230,683 | 10/1980 | Decker et al. | 424/12 |
| 4,243,749 | 1/1981 | Sadeh et al. | 424/12 |
| 4,258,001 | 3/1981 | Pierce et al. | 422/56 |
| 4,363,634 | 12/1982 | Schall, Jr. | 435/180 |
| 4,678,601 | 7/1987 | Ham et al. | 252/518 |
| 4,806,272 | 2/1989 | Wiley | 252/511 |
| 4,810,655 | 3/1989 | Khalil et al. | 436/178 |
| 4,818,437 | 4/1989 | Wiley | 252/511 |
| 4,818,438 | 4/1989 | Wiley | 252/502 |
| 4,925,268 | 5/1990 | Iyer et al. | 128/634 |
| 4,938,860 | 7/1990 | Wogoman | 204/418 |
| 4,987,075 | 1/1991 | Nentwig et al. | 435/288 |
| 4,994,385 | 2/1991 | Beiniarz et al. | 435/964 |
| 5,147,777 | 9/1992 | Sutton et al. | 422/56 |
| 5,160,418 | 11/1992 | Mullen | 435/817 |
| 5,200,051 | 4/1993 | Cazzette et al. | 204/403 |
| 5,231,028 | 7/1993 | Mullen | 435/288 |

FOREIGN PATENT DOCUMENTS

| | | | |
|---|---|---|---|
| 0326100 | 1/1989 | European Pat. Off. | |
| 1112158 | 12/1989 | Japan | G01N 33/543 |
| 2230865 | 10/1990 | United Kingdom | |

OTHER PUBLICATIONS

J. Wang, K. Varughese, Polishable and Robust Biological Electrode Surfaces, Feb. 1, 1990, *Analytical Chemistry*, vol. 62, No. 3.

J. Wang, D. Leech, M. Ozsoz, S. Martinez, One–step fabrication of glucose sensors based on entrapment of glucose oxidase within poly(ester–sulfonic acid) coatings, Sep. 11, 1990, *Analytical Chimica Acta*, 245 (1991) 139–143, Elsevier Science Publishers V.V., Amsterdam.

C. Galiatsatos, Y. Ikaryiama, J. E. Mark, W. R. Heineman, Immobilization of Glucose Oxidase in a Poly [Vinyl Alcohol] Matrix on Platinized Graphite Electrodes by Gamma–Irradiation, *Biosensors & Bioelectronics* 5 (199) 47–61.

A. D. Adler, et al., On the preparation of metalloporphyrins, *J. inorg. nucl. Chem.*, 1970, vol. 32, pp. 2443 to 2445.

*Primary Examiner*—Christopher L. Chin
*Attorney, Agent, or Firm*—John F. Levis

[57] ABSTRACT

The present invention provides an immobilization medium which can immobilize bioreagents to support materials and which dries to a water resistant layer or film. The immobilization medium comprises (i) a liquid or fluid binding reagent and (ii) complexes of a bioreagent immobilized to a solid phase which are evenly dispersed within the binding reagent. The suspension can further include supplemental ingredients evenly dispersed throughout the medium which can provide the medium with electrochemical properties, enhance the stability of the immobilized bioreagent and/or improve the medium's capability of drying to a substantially water resistant or insoluble layer. The immobilization medium provided by the instant invention is in the form of a homogeneous liquid suspension.

15 Claims, 2 Drawing Sheets

BIOREAGENT IMMOBILIZATION MEDIUM

FILED OF THE INVENTION

The present invention relates to the immobilization of bioreagents. In particular, the present invention relates to a homogeneous dispensable suspension for the immobilization of bioreagents.

BACKGROUND OF THE INVENTION

Various binding assays using an immobilized or an immobilizable member of a specific binding pair have been proposed which accomplish the desired separation of a bound and a free form of a labeled reagent. In particular, a number of such binding assays have been described wherein an antibody to an antigen to be detected is bound to an immobilizing material such as the inner wall of a test tube or a plastic bead. For example, U.S. Pat. No. 4,243,749 discloses a competitive binding assay wherein a reaction is carried out in a test tube having a specific antibody to a hapten under determination insolubilized or immobilized on the inner wall of the test tube. The reaction includes a labeled hapten conjugate wherein the quantity of the labeled hapten conjugate, which becomes bound to the test tube wall, is inversely proportional to the amount of the hapten under determination. Similarly, U.S. Pat. No. 4,230,683 discloses a method employing a polystyrene bead having antigen or antibody bound thereto wherein the antigen or antibody is reacted with a hapten-conjugated antibody to the antigen or antibody. The bound hapten-conjugated antibody is further reacted with labeled anti-hapten antibody in order to determine the mount of antigen or antibody in a test sample.

Immobilized catalytically-active-molecules such as enzymes have been used as binding participants to determine the presence or amount of the immobilized enzyme's substrate that may be present in a test sample. Commercial chemistry analyzers use enzymes, which have been bound to porous surfaces, for the conversion of enzyme substrates to optically or electrochemically detectable products. Optical analyzers have been described which have tubular nylon flow cells having enzyme immobilized to the inner walls of the tubing. Optical analyzers which have flow cells containing chromatographic particles (eg, microporous glass) having enzyme immobilized thereon have also been described.

Electrochemical sensors have been described which utilize the ability of an immobilized enzyme to form an electrochemically active molecule as a result of the action of the enzyme on its substrate. Such sensors include certain amperometric electrodes that consist of an enzyme electrode, a reference electrode, a counter electrode and a potentiostat. The enzyme electrode is typically made of platinum and is supplied with an overlaying oxidase enzyme layer. When the electrode is immersed in a sample containing an oxidizable substrate and molecular oxygen, both molecules diffuse into the enzyme layer where the substrate reacts with the enzyme which results in reduction of the enzyme. The reduced enzyme is oxidized by the molecular oxygen which, in turn, is reduced to peroxide. At a sufficiently high electrode potential (measured via the reference electrode), the platinum portion of the enzyme electrode oxidizes the peroxide to regenerate the oxygen and produce two free electrons. The free electrons flow from the enzyme electrode to the counter electrode which completes the circuit consisting of the three electrodes. The potentiostat, which is connected to the circuit, is able to measure the current generated by the electrons and the current measured is related to the amount of oxidizable substrate in the sample. Hence, the presence and/or amount of an oxidizable substrate in the sample can be determined.

Currently available amperometric electrodes which have enzyme electrodes suffer limitations associated with their manufacture. These limitations are generally traceable to the expensive components used to manufacture such electrodes and/or the complex processes used to manufacture them.

For example, U.S. Pat. No. 4,987,075 discloses an enzyme electrode comprising a platinum electrode having a layer of enzymes, which are bound to cellulose with isocyanate monomers and polyurethane polymers, applied thereon. However, the enzyme electrode requires a separate platinum electrode to complete the amperometric electrode.

The immobilization of enzymes directly onto electrode surfaces has also been described. For example, the immobilization of enzymes on platinum surfaces using synthetic polymers has been described (Great Britain Patent Number 2,230,865); sulfonated polyester polymers containing entrapped glucose oxidase has also been used to coat platinum surfaces (*Analytic Chimica Acta*, 245, 139–143 (1991)); physically entrapped enzyme in gamma irradiated polyvinyl alcohol matrices on platinized graphite electrodes has been described (*Biosensors and Bioelectronics*, 5, 47–61 (1990)); a glucose biosensor electrode in which enzyme is incorporated in a silicone water based elastomer has been described (U.S. Pat. No. 4,938,860); and a multilayer microfabrication process by which enzyme electrodes can be manufactured on a silicon wafer has been described (U.S. Pat. No. 5,200,051). However, as mentioned above, such electrodes are expensive and unsuited for mass production.

Another method of manufacturing an enzyme electrode incorporates enzymes into a matrix containing both the electrode material and the enzyme (*Anal. Chem.*, 62, 318–320 (1990)). However, the electrode produced in the manner therein described, must be periodically regenerated by polishing the electrode to expose fresh enzyme.

A further method for manufacturing enzyme electrodes has been described in U.S. Pat. No. 5,160,418. The electrode therein described is made with a suspension consisting of an enzyme adsorbed to finely divided platinized carbon which is added to a low temperature binding agent such as gelatin or hydroxyethyl cellulose. The suspension is then deposited on an electrically conductive carbon paper and allowed to dry. However, the binding agents are water soluble and, as a result, the suspension dissolves when it is immersed in an aqueous sample. Hence the electrode is not reusable.

SUMMARY OF THE INVENTION

According to the present invention, an immobilization medium is provided which is capable of immobilizing bioreagents and which dries to a water resistant layer or film. In particular, the immobilization medium is in the form of a dispensable homogeneous liquid suspension comprising (i) a liquid or fluid binding reagent and (ii) complexes of a bioreagent immobilized to a solid phase which are evenly dispersed within the binding reagent. The suspension can further include supplemental ingredients evenly dispersed throughout the medium which can provide the medium with electrochemical properties, enhance the stability of the immobilized bioreagent and/or improve the medium's capability of drying to a substantially water resistant or insoluble layer.

The immobilizing medium of the present invention can be employed in essentially any assay format which utilizes an immobilized bioreagent. According to one embodiment of the present invention, an enzyme electrode can be manufactured by applying the immobilizing medium herein provided to a support material to form a water insoluble layer thereon. The enzyme electrode can then be used in conjunction with a counter and reference electrode to electrochemically detect the bioconversion of the enzyme's substrate.

According to another embodiment of the invention, the immobilization medium comprising the binding reagent and immobilized enzyme can be applied to a surface to form a biosensor which is capable, via non-electrochemical means, of detecting the bioconversion of the enzyme's substrate.

According to another embodiment of the present invention the immobilizing reagent can be applied to a solid support for use in heterogeneous immunoassay formats known in the art.

DETAILED DESCRIPTION OF THE INVENTION

The following definitions are applicable to the invention:

Definitions

The term "analyte", as used herein, refers to the compound or composition to be detected or measured and which has at least one epitope or binding site. The analyte can be any substance for which there exists a naturally occurring binding member or for which a binding member can be prepared. Analytes include, but are not intended to be limited to, toxins, organic compounds, proteins, peptides, microorganisms, amino acids, carbohydrates, nucleic acids, hormones, steroids, vitamins, drugs (including those administered for therapeutic purposes as well as those administered for illicit purposes), virus particles and metabolites of or antibodies to any of the above substances. For example, such analytes include, but are not intended to be limited to, ferritin; creatinine kinase MB (CK-MB); digoxin; phenytoin; phenobarbitol; carbamazepine; vancomycin; gentamycin; theophylline; valproic acid; quinidine; leutinizing hormone (LH); follicle stimulating hormone (FSH); estradiol, progesterone; IgE antibodies; vitamin B2 micro-globulin; glycated hemoglobin (Gly. Hb); cortisol; digitoxin; N-acetylprocainamide (NAPA); procainamide; antibodies to rubella, such as rubella-IgG and rubella-IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti hepatitis B core antigen IgG and IgM (Anti-HBC); human immune deficiency virus 1 and 2 (HTLV); hepatitis B e antigen (HBeAg); antibodies to hepatitis B e antigen (Anti-HBe); thyroid stimulating hormone (TSH); thyroxine (T4); total triiodothyronine (Total T3); free triiodothyronine (Free T3); carcinoembryoic antigen (CEA); and alpha fetal protein (AFP); and drugs of abuse and controlled substances, including but not intended to be limited to, amphetamine; methamphetamine; barbiturates such as amobarbital, secobarbital, pentobarbital, phenobarbital, and barbital; benzodiazepines such as librium and valium; cannabinoids such as hashish and marijuana; cocaine; fentanyl; LSD; methapualone; opiates such as heroin, morphine, codeine, hydromorphone, hydrocodone, methadone, oxycodone, oxymorphone and opium; phencyclidine; and propoxyhene. The term "analyte" also includes any antigenic substances, haptens, antibodies, macromolecules and combinations thereof.

The term "analyte analog", as used herein, refers to a substance which cross-reacts with an analyte-specific binding member, although it may do so to a greater or lesser extent than does the analyte itself. The analyte-analog can include a modified analyte as well as a fragmented or synthetic portion of the analyte molecule, so long as the analyte-analog has at least one eptopic site in common with the analyte of interest. An example of an analyte-analog is a synthetic peptide sequence which duplicates at least one epitope of the whole molecule analyte so that the analyte-analog can bind to an analyte-specific binding member.

The term "bioconversion", as used herein, refers to the transformation of matter from one form to another. The action of an enzyme on its substrate to produce a transformed substrate is an example of bioconversion.

The term "detectable moiety", as used herein, refers to any compound or conventional detectable chemical group having a detectable physical or chemical property and which can be used to label a binding member to form a conjugate therewith. Such detectable chemical group can be, but is not intended to be limited to, enzymatically active groups such as enzymes, enzyme substrates, prosthetic groups or coenzymes; spin labels; fluorescent molecules such as fluorescers and fluorogens; chromophores and chromogens; luminescent molecules such as luminescers, chemiluminescers and bioluminescers; phosphorescent molecules; specifically bindable ligands such as biotin and avidin; electroactive species; radioisotopes; toxins; drugs; haptens; DNA; RNA; polysaccharides; polypeptides; liposomes; colored particles and colored microparticles and the like.

"Specific binding member", as used herein, means a member of a specific binding pair, i.e., two different molecules where one of the molecules through chemical or physical means specifically binds to the other molecule. In addition to antigen and antibody specific binding pairs, other specific binding pairs include, but are not intended to be limited to, avidin and biotin, carbohydrates and lectins, complementary nucleotide sequences, complementary peptide sequences, effector and receptor molecules, an enzyme cofactor or substrate and an enzyme, an enzyme inhibitor and an enzyme, a peptide sequence and an antibody specific for the sequence or the entire protein, polymeric acids and bases, dyes and protein binders, peptides and specific protein binders (e.g., ribonuclease, S-peptide and ribonuclease S-protein),and the like. Furthermore, binding pairs can include members that are analogs of the original binding member, for example, an analyte-analog or a binding member made by recombinant techniques or molecular engineering. If the binding member is an immunoreactant it can be, for example, a monoclonal or polyclonal antibody, a recombinant protein or recombinant antibody, a chimeric antibody, a mixture(s) or fragment(s) of the foregoing, as well as a preparation of such antibodies, peptides and nucleotides for which suitability for use as binding members is well known to those skilled in the art.

The term "test sample", as used herein, refers to a material suspected of containing the analyte. The test sample can be used directly as obtained from the source or following a pre-treatment to modify the character of the sample. The test sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid and the like, and fermentation broths, cell cultures, and chemical reaction mixtures and the like. The test sample can be pretreated prior to use, such as preparing plasma from blood, diluting viscous fluids, and the like. Methods of treatment can involve filtration, distillation, concentration, inactivation of interfering components, and the addition of reagents. In addition to biological or physiological fluids, other liquid samples can be used such as water, food products and the like for the performance of environmental or food production assays. In addition, a solid material suspected of containing the analyte can be used as the test sample. In some instances, it may be beneficial to modify a solid test sample to form a liquid medium or to release the analyte.

I. IMMOBILIZATION MEDIUM

The immobilization medium of the present invention is in the form of a dispensable homogeneous liquid suspension comprising (a) a bioreagent immobilized to a solid phase and (b) a binding reagent comprising a latex resin, wherein the immobilized bioreagent is evenly dispersed. The immobilization medium may also include supplemental ingredients which enhance the medium's characteristics to obtain a desired performance. Collectively, the components of the mixture form a fluid that resembles paint whereby it has a similar consistency as paint and is easily applied to the surface of a support material. In addition, when the mixture dries, it forms a film that is water insoluble and immobilizes the components of the mixture to the surface to which it has been applied. It is to be understood that the immobilization medium of the present invention enables the permanent immobilization of a bioreagent to a support material.

As a consequence of the medium's ability to form a film that is water insoluble and thereby able to permanently immobilize a bioreagent to a support material, the medium can advantageously be used to provide, for example, biosensor enzyme electrodes which are reusable. As it will be understood, of course, any article made with the immobilization medium herein provided is reusable.

A. Solid Phase

According to the present invention, the solid phase can be any solid material which is comprised of, for example, a carbohydrate, an inorganic material, an organic material, a synthetic organic material, or combinations of the above materials to which a bioreagent is capable of being immobilized and which is capable of substantially even dispersion in the immobilizing mixture, preferably a finely divided solid material. Organic materials from which such solid phase can be selected include, but are not intended to be limited to agarose; agarose derivatives containing amino, carboxyl, epoxy or hydrazide functional groups; polyacrylamide; polyacrylamide derivatives containing amino, carboxyl, epoxy or hydrazide functional groups; and the like. Inorganic solid phase materials can include silicas; aluminosilicates (eg., Zeolites); aluminum oxides; carbon or graphite particles; carbon or graphite particles to which are adsorbed platinum group metals such as platinum, paladium or rhodium; carbon or graphite particles to which are adsorbed platinum group metal oxides; inorganic materials to which primary, secondary, or tertiary amine functional polymers have been adsorbed; inorganic materials to which quaternary ammonium polymers such as Merquat® (Quaternium -40) have been adsorbed; and the like. Moreover, combinations of inorganic and organic materials from which the solid phase can be selected include, but are not intended to be limited to carbon or graphite particles to which are adsorbed metalloporphyrins such as, for example, cobalt protoporphyrin. Preferably, the solid phase comprises finely divided particles which are less than about 25 μ in size and have a surface area of at least about 200 m²/g. Solid phases having a particle size of less than about 0.1 μ are particularly preferred. As it will be understood by one skilled in the art, the size of a particular solid phase may be greatly reduced once it is dispersed in the binding reagent. It will therefore be understood, of course, that the original size of a solid phase is not intended to limit the invention herein provided.

One advantage of using finely divided solid phases is that such a solid phase has a high capacity for immobilizing biopolymers thereto. As a result, several bioreagents can be bound to a single solid phase particle. In this manner, biological activity can be increased while decreasing the amount of solid phase dispersed in the binding reagent. Additionally, the use of a finely divided solid phase enhances the texture of the layer or film which forms after the medium herein provided has dried.

B. Bioreagents

The bioreagent of the present invention includes, but is not intended to be limited to, analytes, analyte analogs, specific binding pair members, detectable moieties, and the like. It is to be understood that the bioreagent will of course depend upon the use for which the immobilizing reagent is intended. For example, in the case of an enzyme electrode, the bioreagent is an enzyme and the immobilization medium is applied to a support material as described herein. Such enzymes include, but are not intended to be limited to, glucose oxidase, glutamate oxidase, lactate oxidase, glycerol phosphate oxidase, cholesterol oxidase, cholesterol esterase, lipase, glycerol kinase, glutamate dehydrogenase, creatinine deaminase, or uricase. In the case of an immunoassay, the bioreagent can be a member of a specific binding pair.

II. IMMOBILIZATION OF BIOREAGENTS TO A SOLID PHASE

The bioreagent can be attached to the solid phase according to methods well known in the art. Such methods include, but are not intended to be limited to, adsorption, ionic binding, covalent binding, and the like.

A. Adsorption of Bioreagents to the Solid Phase

A bioreagent can be immobilized to a solid phase by adsorption of the bioreagent to the solid phase to form a solid phase/bioreagent complex. Generally, adsorbing a bioreagent to the solid phase is accomplished according to methods well known in the art. It will be understood, of course, that the adsorptive properties displayed by bioreagents toward solid phases is a function of the pH and ionic strength of the buffer containing the two entities. Thus, it will also be understood, of course, that in order to achieve proper adsorption, the pH and ionic strength of a buffer containing a bioreagent and solid phase may vary according to the specific bioreagent and/or specific solid phases being used. Preferably, the bioreagent is dissolved in a solid phase mixture such that its concentration in the solution will saturate the non-specific binding sites on the surface of the particular solid phase. Thus, the pH and ionic strength of the buffer is preferably such as will allow maximal adsorption of the bioreagent to the solid phase.

B. Ionic Immobilization of Bioreagents to the Solid Phase

Immobilization of a bioreagent to a solid phase can generally be accomplished by exploiting the attractive forces associated with a charged bioreagent and an oppositely charged solid phase, to thereby form a solid phase/ bioreagent complex. Preferably, a cationic solid phase, wherein a positively charged compound is adsorbed or covalently bound to the solid phase, is reacted with an anionic bioreagent to obtain a solid phase/bioreagent complex. Compounds which are suitable for conferring a positive charge upon a solid phase include, but are not intended to be limited to, quaternary ammonium polymers such as Merquat® (Quaternium-40); amine functional polymers such as polyethylene-imine; and the like.

Adsorption of these compounds to the solid phase readily occurs by adding an excess of the compound, dissolved in a suitable solvent, to the solid phase. After a sufficient time has elapsed, the solid phase can be collected, for example, by filtration or centrifugation. Any residual compound can be separated from the solid phase by rinsing the solid phase with a suitable solvent, then re-collecting the solid phase. The rinsed solid phase can then be used wet or can be dried before a biopolymer is ionically bound to it.

Although there are anionic bioreagents (eg. enzymes and proteins) that will inherently ionically bind a cationic solid phase, it is preferable to anionically modify an enzyme or a protein so that more ionic bonds can be formed between the enzyme or protein and the solid phase.

One method for providing a negative charge to, for example, an enzyme or protein is by reacting it with, for example, an aliphatic or aromatic carboxylic acid anhydride. Such carboxylic acid anhydrides include, but are not intended to be limited to pyromellitic dianhydride, succinic anhydride, maleic anhydride, and the like.

According to a preferred embodiment, a negative charge is provided to, for example, an enzyme or protein by reacting pyromellitic dianhydride with positively charged amino groups, wherein the amino groups present on the enzyme or protein can be converted to aromatic tricarboxylates which have three negative charges. This conversion can be carried out by adding an aqueous suspension of pyromellitic dianhydride to a solution of enzyme or protein. Preferably, the enzyme or protein is dissolved in an appropriate buffer having a pH in the range of between about 6.5 and about 8.0, preferably in the range of between about 7.0 and about 7.5. The quantity of pyromellitic dianhydride can be from between about 0.05 and about 0.5 times more than the quantity of the biopolymer, preferably between about 0.05 and about 0.15 times more than the quantity of the enzyme or protein. Although the conversion of the amino group to the aromatic tricarboxylate is typically complete within about 5 minutes, the reaction is preferably allowed to incubate at an ambient temperature for from between about 10 minutes and about 20 minutes. The reaction mixture can then be added directly to a cationic solid phase or purified before being reacted with a cationic solid phase.

Since the bioreagent and the solid phase carry opposite charges, an ionic bond between the two entities will readily form. Typically, the charged solid phase will have high capacity for binding an anionically charged bioreagent. Preferably, the bioreagent is at a concentration that will saturate the cationic binding sites on the solid phase. When a suspension of cationically charged solid phase is added to a solution of anionically charged bioreagent to form a reaction mixture, it is preferred that the ratio of bioreagent to solid phase is in the range of from between about 1:1.5 and about 1:5. The reaction is preferably carried out in a low ionic strength buffer which has a pH of from between about 6.5 and about 7.5, for from between about 1 minute and about 30 minutes, and at a temperature of from between about 2° C. and about 25° C. The bioreagent/solid phase complex thus formed can be separated from the unbound bioreagent by methods well known to those skilled in the art, and either added to the binding reagent or left in the reaction mixture, and then added directly to the binding reagent. In cases where the complexes are separated from the reaction mixture, the reaction mixture can be filtered using a filter having a pore size small enough to trap the bioreagent/solid phase complexes, yet large enough to allow unbound bioreagent to flow through the filter. Alternatively, the complexes can be centrifuged to form a wet pellet. To ensure that all of the unbound bioreagent is removed from the complexes, the captured complexes can be washed with low ionic strength buffer having a pH from between about 6.0 and about 7.5.

Alternatively, a bioreagent and solid phase can be ionically bound and co-precipitated from a solution in a single step. Generally, this precipitation is accomplished by first making a single solution of bioreagent and solid phase, treating the solution with pyromellitic dianhydride, and then treating the solution with one of the positively charged polymers described above. Preferably, the ratio of bioreagent to solid phase is from between about 1:1 and about 1:5 and the quantity of pyromellitic dianhydride in the solution is from between about 0.05 and 0.15 times the quantity of the bioreagent in the solution.

It is to be understood, of course, that the manner by which a biopolymer can be ionically bound to a solid phase is not intended to be limited to the methods described herein, and that other methods known in the art can be employed as well.

C. Covalent Immobilization of Bioreagent to the Solid Phase

A bioreagent can be immobilized to a solid phase by a covalent bond which is formed between the bioreagent and the solid phase to form a bioreagent/solid phase complex. In order to form such a covalent bond, the solid phase can be modified to enable it to form a covalent bond with a bioreagent. Such modifications to the solid phase include, but are not intended to be limited to, adding functionalities such as amine groups, carboxylate groups, epoxide groups, and the like, to the solid phase. For example, silica can be derivatized with aminopropyl triethoxy silane or polyethylene-imine, using methodologies well known to those skilled in the art. After such modification has been completed, the aminated solid phase can be further derivatized to introduce other functional groups by methods well known in the art. Bioreagents can then be covalently bound to a derivatized solid phase using methods well known in the art. For example, use of a water soluble carbodiimide such as 3 ethyl 1-(3-dimethylaminopropyl) carbodiimide, or a similar carboxylate activating agent, can be added to an appropriate buffer containing a modified solid phase and a bioreagent to yield a covalently bound bioreagent/solid phase complex which is formed via an amide bond between the carboxylate and amino groups.

Alternatively, a modified solid phase can be reacted, as above, with a modified enzyme. Such modified enzymes include, but are not intended to be limited to, those modified with pyromellitic dianhydride as described previously, or other mono- or polyanhydrides, such as N-carboxy-alpha-amino acid anhydrides, and the like using methods well known in the art.

In another method of covalently binding the biopolymer to the solid phase, heterobifunctional coupling compounds, which are well known in the art, can be used. Such compounds include, but are not intended to be limited to, m-maleimidobenzoyl-N-hydroxysuccinimide ester (MBS), sulfosuccinimidyl 4-(p-maleimidophenyl) butyrate (S-SMPB), m-maleimidobenzoylsulfosuccinimide ester (S-MBS), N-γ-maleimidobutyryloxysuccinimide ester (GMBS), succinimidyl 4-(N-maleimidomethyl) cyclohexane 1-carboxylate (SMCC), those found in U.S. Pat. No. 4,994,385, and the like. Methods of using such compounds to covalently couple two compounds is well known in the art.

It is to be understood, that according to the present invention, one or more species of bioreagents can be immobilized to a solid phase. For example, different antibodies, that are specific for their respective antigens, can be immobilized to a single solid phase. As another example, different enzymes, that are specific for their respective substrates, can be immobilized to a single solid phase.

It is to be understood, of course, that the manner by which a bioreagent can be covalently bound to a solid phase is not intended to be limited to the methods described herein, and that other methods known in the art can be employed as well.

III. BINDING REAGENT

After a bioreagent has been immobilized to a solid phase to form a bioreagent/solid phase complex as described herein, the bioreagent/solid phase complex is combined with a binding reagent to form the immobilization medium of the present invention. The binding reagent is in a liquid or fluid form wherein the bioreagent/solid phase complexes are evenly dispersed therein. The binding reagent enables the bioreagent/solid phase complexes to irreversibly adhere to the surface of a support material when dried thereon. It has been unexpectedly and surprisingly discovered that the binding reagent, according to the present invention, dries to a physically durable water resistant layer which retains the biological activity of the bioreagent. In addition, the binding reagent will adhere to a variety of surfaces, including, but not intended to be limited to smooth or non-porous, as well as porous surfaces.

It is to be understood, that since the binding reagent is fluid, the immobilization medium of the present invention can be readily dispensed or applied to a support material by various methods. Thus, for example, the immobilization medium can be dispensed or applied to a support material by brushing, pumping, liquid metering, screen printing, spraying, jetting or dipping the support material into the immobilization medium. Furthermore, since the immobilization medium can be dried at ambient temperatures, the bioreagent/solid phase complexes dispersed throughout the medium are not exposed to harsh temperatures that may denature the bioreagent component. Still further, a surface to which the immobilization medium has been applied and dried, is reusable because the immobilization medium dries to a water resistant adherent layer. Moreover, the binding reagent is not limited by the types of surfaces to which it is applied.

The binding reagent according to the present invention is a latex resin. Latex resins contemplated by the present invention include, but are not intended to be limited to, acrylic latex, vinyl acetate latex, styrene acrylic latex, polyurethane latex, and the like, and two or more thereof. The binding reagent may also contain supplemental ingredients which can provide the medium with electrochemical properties, enhance the stability of the immobilized bioreagent and/or improve the mediums capability of drying to a substantially water resistant or insoluble layer. Such supplemental ingredients include, but are not intended to be limited to, plasticizers, thickeners, film forming agents, stabilizers, dispersing agents, defoaming agents, electrochemically active agents and the like. Examples of such optional ingredients include, but are not intended to be limited to, plasticizers such as dibutyl phthalate and dioctyl sebacate; thickeners such as hydroxyethylcellulose, silica and Acrysol SCT 200; film forming agents such as 2-ethoxyethanol, ethyleneglycol monopropyl ether and 2-(2-butoxyethoxy) ethanol; stabilizers such as sucrose, trehalose, dextran and polyethylene glycol; dispersing agents such as Trition X-100® detergent; defoaming agents such as 2-octanol; and electrochemically active agents such as platinized carbon or platinized graphite and the like.

It will be understood, of course, that the compounds and amounts thereof which comprise the immobilizing reagent will depend upon the particular solid phases added, the dispensing processes used or the characteristics of the drying and curing steps. For instance, plasticizers may be required to prevent cracking of the coating; thickeners may be desirable to prevent settling of the suspended solids; film forming agents, typically organic solvents, may be required to solubilize plasticizers and control the rate of drying so that smooth coatings result; stabilizers may be required to promote biopolymer stabilization during and after the drying process; dispersing agents may be required to prevent polymer aggregation; defoaming agents may be required to reduce foaming during mixing; and electrochemically active agents may be required to allow the immobilization medium electrically and/or electrochemically active. Particular compounds and amounts thereof which can be used to facilitate plasticizing, thickening, film forming, dispersion, defoaming and conductivity are well known in the latex paint industry and within the knowledge of one of ordinary skill in the art.

The optimum amount of bioreagent/solid phase complexes and supplemental solids which can be added to the binding reagent is a function of the critical pigment volume concentration (CPVC) of the immobilization medium. As would be understood by one skilled in the art, CPVC refers to a relationship between a binding reagent and the amount of pigment (particles) contained therein. Binding reagents that are below the CPVC form a coating that has a continuous binding reagent phase in which the particles are imbedded, but are not in contact with each other. Conversely, binding reagents that are above the CPVC do not have a continuous binding reagent phase but the particles imbedded therein are in contact.

The physical properties associated with a coating formed with a reagent above the CPVC are different than a coating formed with a reagent below the CPVC. For example, properties such as electrical and barrier transport, density, and mechanical strength are affected by the CPVC. According to the present invention, it has been unexpectedly and surprisingly found that, when the amount of suspended solids in the binding reagent are substantially higher than the CPVC, electrical conductivity and permeability of the coating is optimized without compromising the physical strength of the coating.

It is to be understood that a suspension of the solid phase/bioreagent complex can be added directly to the binding reagent or collected and washed before adding to the binding reagent. It is to be understood, of course, that the method of physical dispersion of the bioreagent/solid phase material in the binding reagent can affect the properties of the films produced by the immobilization medium. It is therefore preferred that the bioreagent/solid phase complexes are well dispersed in the binding reagent in order to form a homogeneous mixture. Methods for dispersing the complexes include, but are not intended to be limited to high shear homogenization, ball milling and the like.

It is to be understood that one or more different species of bioreagent/solid phase complexes can be dispersed throughout the binding reagent when forming the immobilizing medium according to the present invention. For example, one type of enzyme immobilized to a solid phase can be added to an immobilization medium containing a second type of enzyme immobilized to a solid phase. Similarly, an antibody specific for one antigen immobilized to a solid phase can be added to immobilization medium that contains an antibody specific for a different antigen immobilized to a solid phase. It is also to be understood, of course, that such addition can be simultaneous or sequential.

IV. SUPPORT MATERIALS

Generally, support materials according to the present invention include, but are not intended to be limited to, beads, magnetic particles, micro or macro particles, tubing, test tubes, microtiter plates, electrochemical materials, membranes, and the like. Such support materials can be made from synthetic materials, naturally occurring materials, or naturally occurring materials which have been synthetically modified, and include, but are not intended to be limited to, cellulose materials, such as paper, cellulose and cellulose derivatives such as cellulose acetate and nitrocellulose; fiberglass; naturally occurring cloth such as cotton; synthetic cloth such as nylon; porous gels such as silica, agarose, dextran, and gelatin; porous fibrous matrixes; starch based materials such as cross-linked dextran chains; ceramic materials; olefin or thermoplastic materials including polyvinyl chloride, polyethylene, polyvinylacetate, polyamide, polycarbonate, polystyrene, copolymers of vinyl acetate and vinyl chloride, combinations of polyvinyl chloride-silica; and the like.

It will be understood, of course, that the support material to which the immobilization medium is applied should be capable of supporting the immobilization medium, and the surface should be suitable for the purpose for which the support material is intended. For example, if the immobilization medium is to be used for an amperometric or potentiometric electrode application, the surface can preferably be one that is, or has in conjunction with it, an entity that is electrochemically conductive. Such support materials include, but are not intended to be limited to, copper; platinum; gold; palladium; titanium; titanium coated with conductive carbon or graphite inks; conductive plastics and the like.

According to the present invention, a single surface can be coated with more than one coating of the immobilization medium. In particular, a surface can be coated with more than one layer of the same immobilization medium or a surface can be coated successively with two or more different types of immobilization medium. For example, an immobilization medium containing cholesterol oxidase/solid phase complexes can be applied to a platinized carbon support material, and then, after a period of drying, a second immobilization medium containing cholesterol esterase/solid phase complexes can be applied thereto and dried to form an enzyme electrode for determining the amount of cholesterol in a test sample.

V. BIOREACTORS AND BIOSENSORS

According to the present invention, a bioreactor can be prepared by applying the immobilization medium of the present invention to a surface that is not involved in detection of the product of a reaction. According to this embodiment, the presence and/or amount of a substrate in a sample can be determined photometrically by adding an optical indicator material to a sample during or after contact of the sample with dried immobilization medium. An optical indicator can be one that reacts with a by-product of the action of an enzyme on its substrate to produce a change in, for example color, fluorescence and luminescence. Quantitative analysis of the amount of substrate present in a sample can be accomplished by, for example, comparing the color, fluorescence or luminescence produced to that expected for a known amount of substrate. This comparison can be made visually or with an analytical instrument such as a spectrophotometer, fluorometer or luminometer.

The immobilization medium of the present invention can also be employed for the preparation of biosensor devices, in which the reaction of the enzyme substrate is monitored directly by an electrochemical or optical sensor. Electrochemical biosensors can be prepared by applying or dispensing the immobilization medium of the present invention, which contains an electrically conductive and/or electrochemically active solid phase, to an electrically conductive support material and permitting it to dry as described herein. It will be understood, of course, that the electrically conductive and/or electrochemically active solid phase can have biopolymer immobilized thereon or such a solid phase could be added, as a supplemental ingredient, to an immobilization medium containing biopolymer/solid phase complexes. It will also be understood, of course, that an immobilization medium containing, for example, an enzyme/solid phase complex can be applied as an overcoating to an electrochemically active sensor device to produce a biosensor.

Such a support material having immobilization medium dried thereon can then be used in conjunction with amperometric or potentiometric detection devices to measure the current or potential produced by such a support material when contacted with a test sample. The configuration of such a device will be readily apparent to those skilled in the art. According to an optical sensor embodiment, the immobilizing reagent can be applied to the surface of an optical sensor, such as the end of a fiberoptic device which can measure reflected or chemically modulated light. For example, the immobilization medium herein provided could be applied to an oxygen sensor capable of optically detecting oxygen concentration as described in U.S. Pat. No. 4,810,655 and U.S. Pat. No. 4,925,268. The consumption of oxygen by an oxidase enzyme could then be measured directly by such a sensor and related to the amount of oxidase co-substrate consumed.

VI. BINDING ASSAYS

According to the present invention, the immobilization medium can also be employed to prepare reagents for use in conventional specific binding assay formats known in the art. Such methods include, but are not intended to be limited to, competitive immunoassays, sandwich immunoassays, immunometric immunoassays, and the like.

Typically, assay reagents for performing such assays may take many different forms, but, in general, comprise (1) the analyte to be detected, (2) a specific binding partner for the analyte, and (3) a labeled reagent. The assay reagents can be combined simultaneously or sequentially, wherein the labeled reagent becomes bound to its corresponding binding partner such that the extent of binding is a function of the amount of analyte present. Typically, the bound species and the free species are physically separated from each other and the amount of label present in either fraction thereof is determined by measuring the activity of the particular label being used. Such separation is often accomplished by immobilizing one of such species to a support material to form a capture reagent. Such a capture reagent can be made by applying an immobilization medium to a support material as described herein. For example, in a competitive heterogeneous immunoassay format, a specific binding partner, such as an antibody, can be immobilized to a support material to form a capture reagent. A reaction mixture is then formed comprising a test sample containing analyte, the capture reagent and a labeled reagent comprising the analyte labeled with a detectable moiety, to form bound and free species as described above, i.e., analyte bound to labeled reagent and labeled analyte bound to the capture reagent. Upon separation thereof, the amount of labeled reagent bound to the analyte or the amount of labeled reagent bound to the capture reagent, can be detected and correlated to the amount of analyte present in the test sample. Similarly, in a sandwich heterogeneous immunoassay format, a test sample containing analyte is contacted with an antibody immobilized to a support material and a labeled reagent comprising an antibody labeled with a detectable moiety to form an immobilized complex comprising the immobilized antibody, the analyte, and the labeled reagent. Upon separation thereof, the amount of labeled reagent in the immobilized complex or the amount of free labeled reagent, can be detected and correlated to the amount of analyte present in the test sample.

Accordingly, a capture reagent for use in such immunoassay formats can be prepared employing the immobilization medium of the present invention by applying the immobilization medium of the present invention to a support material, wherein the immobilization medium comprises, for example, a specific binding member immobilized to a solid phase according to the teachings of the present invention.

It is to be understood that upon completion of an assay, such capture reagent, if desired, may be regenerated for use in a subsequent assay. The regenerative property of the capture reagent is due to the stability of the dried immobilizing reagent used to create such a reagent. Regeneration of the capture reagent can be accomplished by disassociating the bound analyte from the capture reagent according to methods well known in the art.

VII. TEST KITS

Test kits according to the present invention comprise all of the essential reagents required to perform the various assays contemplated herein employing support materials having the immobilization medium of the present invention applied thereto. Such test kits are presented in a commercially packaged form as a combination of one or more containers holding the necessary reagents, as a composition or admixture where the compatibility of the reagents will allow. It is to be understood that the test kit can, of course, include other materials as are known in the art and which may be desirable from a commercial user standpoint, such as buffers, diluents, pre-treatment reagents, and the like.

According to one embodiment, a test kit is provided for performing a heterogeneous immunoassay as described above, wherein the capture reagent employed therein comprises the immobilization medium of the present invention.

The following examples are not intended to limit the invention herein provided but intended to illustrate the invention.

EXAMPLE 1

Production of Glucose Oxidase Enzyme Electrode

Glucose oxidase was immobilized on platinized carbon and the adsorbed enzyme was then incorporated into a coating solution containing a carboxylated polystyrene/acrylic resin (Pliolite resin 7104) and a water soluble sulfonated polyester polymer (AQ55). The formulation was optimized to form a homogeneous mixture which was coated onto a conductive carbon ink surface and tested electrochemically. The AQ55 polymer assists in dispersing the platinized carbon throughout the resin and allowing an adherent coating to form when the resin has dried.

Materials

1. Platinized Vulcan XC 72 (carbon black) containing 10% platinum (E-Tek Inc, Framingham, Mass.)
2. Glucose Oxidase (GOD: Grade I from Aspergillus niger, Boehringer Mannheim Biochemicals, Indianapolis, Ind.)
3. Phosphate Buffered Saline (PBS: 100 mM Na Phosphate, 100 mM NaCl, pH 6.0)
4. AQ 55 polymer (solid form, Eastman Chemicals, Kingsport, Tenn.)
5. Pliolite Waterborne Resin 7104 (Goodyear Chemicals, Akron, Ohio)

Procedure

Platinized carbon (50 mg) was added to PBS buffer (0.4 ml) and homogenized with an OmniMixer 2000 (available from Omni International, Waterbury, Conn.) for 1 minute at maximum speed. A solution of GOD (6.9 mg in 0.1 ml PBS) was added to the platinized carbon to form a suspension which was homogenized as above. The suspension was then allowed to incubate for 1 hour at an ambient temperature before AQ55 polymer (42 mg in 0.15 ml water) was added and the suspension was re-homogenized as above. The resin (0.075 ml of a 44% solids solution) was then added and the suspension was homogenized as previously set forth. Using a paint brush, two coats of the resulting immobilization medium were applied to the surface of a custom made amperometric electrode.

Figure 1:
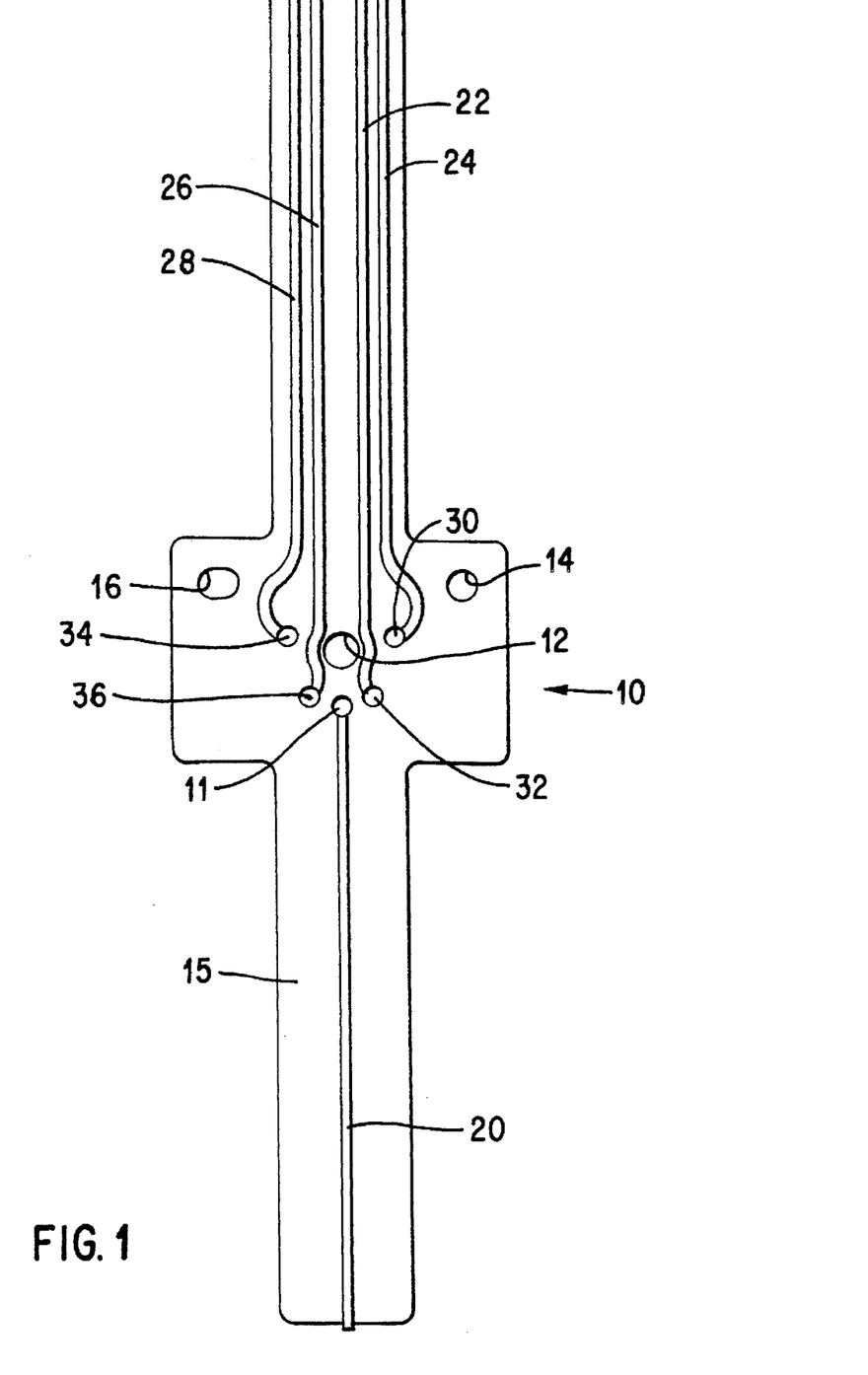
FIG. 1 illustrates a flexible biosensor electrode platform.

Referring now to the drawings, FIG. 1 shows the flexible electrode platform 10 used to create the amperometric electrode used herein. Electrically conductive traces 20, 22, 24, 26, and 28 were made of conductive carbon (available from Acheson Colloids, Fishers, Ind.) and screen printed on the solid substrate 15 which was made of polyester. A 1.0 mm diameter reference electrode 11 was screen printed on top of conductive trace 20 using a silver/silver chloride paint (available from Olin Hunt, Ontario, Calif.) and conductive silver and carbon traces (available from Acheson Colloids) for electrical interface with a potentiostat. Working electrodes were created by applying (with a small paint brush) approximately 0.5 µl of the immobilization medium on top of the conductive traces 22, 24, 26, and 28 to form circular deposits of the medium 30, 32, 34, and 36 having a diameter of approximately 1.0 mm.

Figure 2:
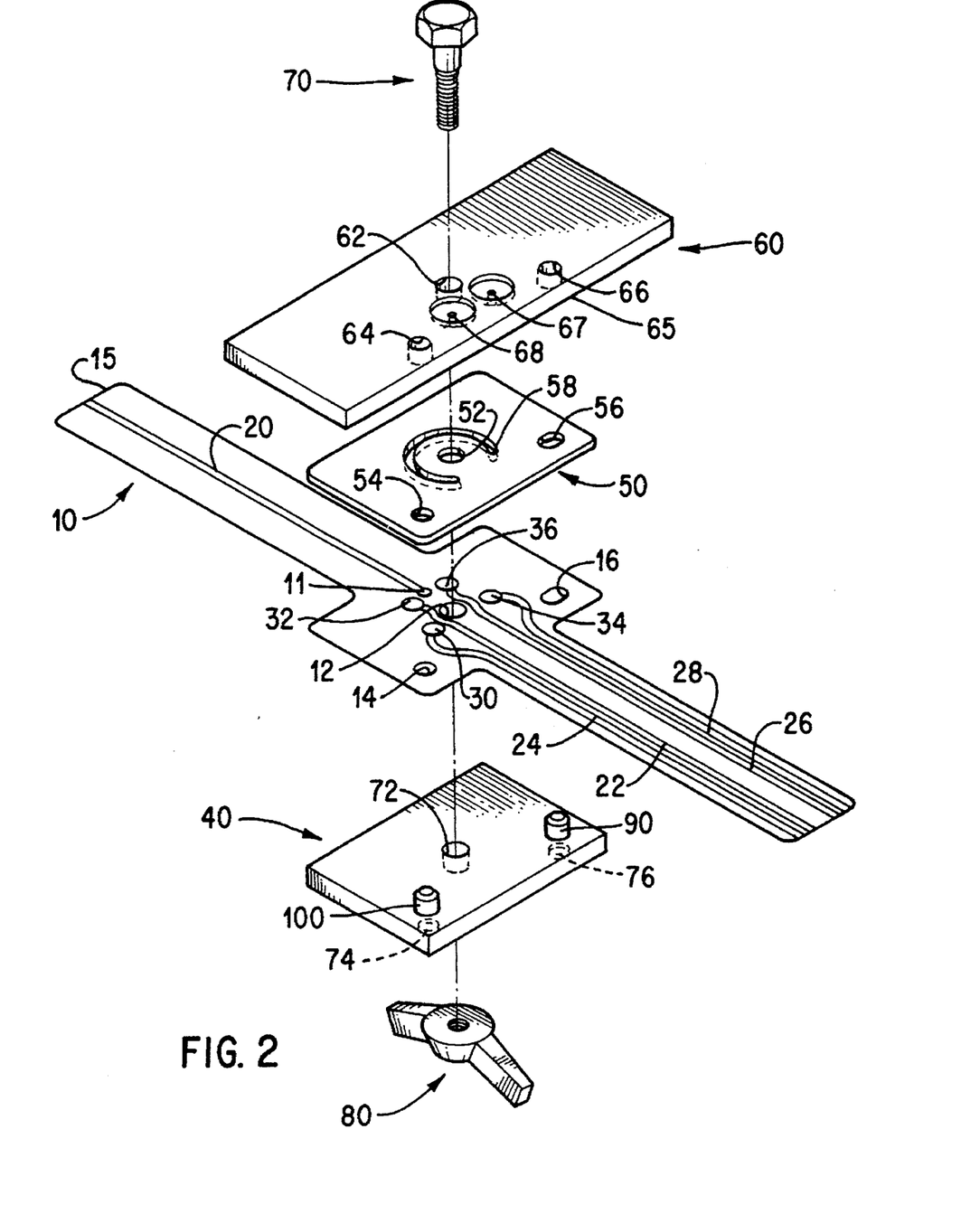
FIG. 2 is an expanded view of an amperometric electrode flow cell assembly.

As shown best in FIG. 2, a screw 70, nut 80, and guide pins 90 and 100 secured the flexible electrode platform 10 and a flexible silastic gasket 50 between a small hard plastic-backing-plate 40 and a large hard plastic-backing-plate 60. In order to allow screw 70 and pins 90 and 100 to extend through all of the above components, small backing plate 40 was supplied with apertures 72, 74 and 76; flexible electrode platform 10 was supplied with apertures 12, 14 and 16; gasket 50 was supplied with apertures 52, 54 and 56; and large backing plate 60 was supplied with apertures 62, 64 and 66.

Gasket 50 also had a channel 58 which, when secured over the working electrodes 30, 32, 34, and 36, and reference electrode 11, formed a 40 μl flow cell. Large backing plate 60 had ports 67 and 68 which, when properly secured next to gasket 50, served as inlet and outlet ports for the flow cell. A counter electrode for the electrochemical cell was created by dispensing a layer of conductive carbon ink 65 (available from Acheson Colloids) on the large backing plate 60.

The completed electrode flow cell was connected to a potentiostat device via conductive traces 20, 22, 24, 26, and 28. The potentiostat measured the current for PBS buffer and a 3 mM glucose calibrator (in PBS) when they were individually pumped into the flow cell with a peristaltic pump. Peak current from the oxidation of hydrogen peroxide (generated from glucose and oxygen by glucose oxidase action) was measured at a working cell potential of 350 mV after the initial charging current dissipated. Net glucose signal was calculated as the difference in current between buffer and glucose signals.

Results

Initially, the glucose electrode generated 1948 nA of current/ram of glucose. The signal declined steadily over a week of testing at ambient temperature, but the coating remained intact. Thus the coating used to produce the electrode was active, rugged and reusable.

EXAMPLE 2

Production of an Enzyme Electrode Using Glucose Oxidase Adsorbed to Platinized Carbon In comparison to Example 1, this coating procedure used a different resin and mixing procedure. The resin (see below) was selected from commercial paint industry formulations designed to be fast drying, adherent and able to emulsify pigments. The mixing procedure was designed to generate high shear rates, thus producing a very highly dispersed pigment and small particle size. In order to obtain this smooth emulsion, the formulation components were mixed in a WIG-L-BUG (Crescent Dental Manufacturing, Lyons, Ill.) which is a device designed to mix dental amalgams. The mixer mechanically agitates the formulation in a 2 ml stainless steel vial containing a ball bearing, thus allowing 0.5 to 1 ml coating preparations to be blended.

Materials
1. Platinized Vulcan XC 72 (carbon black) containing 10% platinum
2. GOD
3. PBS
4. Acrylic resin mix (31.6% non-volatile solids formulated as shown below)

| Acrylic Resin Mix Component | % by weight |
|---|---|
| Joncryl 537 acrylic emulsion (Johnson Wax, Racine, WI) | 54 |
| Joncryl 56 acrylic resin (Johnson Wax, Racine, WI) | 27 |
| DMAMP 80 (Angus Chemical Co., Northbrook, IL) | 1 |
| Ektasolve EP (Eastman Chemicals, Kingsport, TN) | 9 |
| Distilled water | 9 |

Procedure

Enzyme was adsorbed to platinized carbon by adding a solution of GOD in PBS buffer to suspensions of platinized carbon in PBS buffer. One suspension contained 101 mg of platinized carbon in 0.44 ml of PBS plus 0.2 ml of a 50 mg/ml solution of GOD, while the other suspension contained 51 mg of platinized carbon in 0.2 ml of PBS plus 0.1 ml of a 50 mg/ml solution of GOD. The mixtures were allowed to statically incubate for 1.5 hours at an ambient temperature before they were centrifuged at 2000 rpm. The supernatants were discarded and the resulting wet GOD/carbon pellets were resuspended in 0.8 gm of the resin mix and blended in the WIG-LBUG for 10 minutes. The resulting coating solutions were brush painted onto separate electrodes and tested as in Example 1. The formulations for the two coating solutions are shown below in Table 1.

TABLE 1

| Formula | mg carbon | mg Resin Mix | mg Resin Solids | Resin solids/ Carbon ratio |
|---|---|---|---|---|
| 1 | 101 | 800 | 253 | 2.50 |
| 2 | 51 | 800 | 253 | 4.96 |

Results

Both formula 1 and 2 produced coatings with excellent adherence and no cracking or fissuring. Formula 2 was slightly more glossy, due to the increased percentage of resin. The electrodes were tested as in Example 1 for hydrogen peroxide and glucose response, as well as residual background current and electrical resistance. The results of these tests are shown below in Table 2.

TABLE 2

| Formula | Peroxide slope, nA/mM | Glucose Slope, nA/mM | Background, nA (Buffer) | Resistance, ohms |
|---|---|---|---|---|
| 1 | 1900 | 282.6 | 126 | 35–40 |
| 2 | 300 | 22.9 | 58 | |

The above results indicated that the ratio of resin to solids (carbon) in the formulation effected the electrochemical responses to glucose and peroxide but had a minor effect on background current and electrical resistance. Electrical conductivity and permeability of the coating are optimal, but not so high that the physical strength of the coating is compromised, when the carbon (pigment) is close to the Critical Pigment Volume ratio.

EXAMPLE 3

Production of an Enzyme Electrode using Glucose Oxidase Ionically Bound to Silica In this method, soluble silica and enzyme were co-precipitated from a solution with a quaternary polymer. In order to increase the ionic affinity of GOD for the positively charged polymer/silica, GOD was modified with pyromellitic dianhydride, which resulted in little or no loss in GOD activity and helped to stabilize the enzyme against loss of activity at an alkaline pH.

Materials
1. Platinized Vulcan XC 72 (carbon black) containing 10% platinum
2. GOD
3. Modified Phosphate Buffered Saline (MPBS: 100 mM Na Phosphate, 100 mM NaCl, pH 7.4, containing 1 mM ethylene diamine tetra acetate and 0.1% Kathon CG as preservative)
4. Snowtex UP, a 20% soluble colloidal silica solution (Nissan Chemicals, Tokyo, Japan)
5. Pyromellitic Dianhydride (1,2,4,5 Tetra carboxylate dianhydride, Aldrich Chemicals, Milwaukee, Wis.)
6. Magnifloc 591C, a 20% w/w quaternary ammonium polymer in water (American Cyanamid Co., Wayne, N.J.)
7. Acrylic resin mix (8.85% non-volatile solids formulated as shown below)

| Acrylic Resin Mix Component | % by weight |
|---|---|
| Joncryl 537 acrylic emulsion (Johnson Wax, Racine, WI) | 15.5 |
| Dibutyl Phthalate (Fluka Chemical,Buchs, Switzerland) | 1.7 |
| Sodium Hydroxide (3% solution) | 2.1 |
| 2 Ethoxy ethanol (Aldrich Chemicals, Milwaukee WI) | 5.0 |
| Distilled water | 75.7 |

Procedure

GOD (20 mg) was dissolved in 2 ml of MPBS buffer and 0.5 ml of Snowtex UP (100 mg of soluble silica) was added to form a mixture. 0.1 ml of a freshly prepared suspension of Pyromellitic dianhydride (20 mg/ml in water) was then added to the mixture which subsequently turned cloudy. The mixture cleared after about 10 minutes at room temperature, indicating completion of the dianhydride acylation reaction. After the reaction was complete, 0.4 ml of a 20 mg/ml aqueous solution of Magnifloc 591C (8 mg of quaternary ammonium polymer) was added to the reaction mixture. The addition of the Magnifloc solution resulted in the precipitation of the silica and most of the GOD. The precipitate was centrifuged and washed three times with water to remove soluble salts. The final pellet was dried on a frited glass filter with 10 ml of acetone, yielding 89.5 mg of a yellow powder, containing silica, quaternary polymer and GOD.

A GOD/Silica coating reagent was prepared by combining 66.0 mg of dry GOD/Silica above with 934 mg of the above Acrylic resin mix. A platinized carbon (Vulcan XC 72) coating reagent was prepared by combining 66.0 mg of dry platinized carbon with 934.0 mg of Acrylic resin mix. Both were mixed in the WIG-L-BUG for 3 minutes. These two solutions were used to prepare the reagents shown in Table 3. An aliquot (0.4 μl) of each reagent solution was manually deposited (using a glass capillary micropipette) onto working electrodes (as in Example 1) and allowed to dry for 15 hours. The resulting electrodes were tested in a potentiostat at 350 mV, using 0.1 mM hydrogen peroxide and a 5 mM glucose solutions in PBS buffer. Currents were measured at ambient temperature and are shown below in Table 4. The electrodes were stored at ambient temperature in PBS buffer and were retested after 5 days of wet storage. The results obtained after storage are also shown in Table 4.

TABLE 3

| Formula | gm of GOD/Silica reagent | gm of Pt Carbon reagent | Ratio of Carbon/ GOD-Silica | μl of coating solution/ spot |
|---|---|---|---|---|
| 1(C/Si = 1) | 0.105 | 0.110 | 1.05 | 0.4 |
| 2(C/Si = 2) | 0.103 | 0.209 | 2.03 | 0.4 |
| 3(C/Si = 3.5) | 0.117 | 0.413 | 3.53 | 0.4 |

TABLE 4

| | Day 0 Results | | Day 5 Results | |
|---|---|---|---|---|
| Formula | Peroxide response, nA/mM | Glucose Response, nA/mM | Peroxide Response, nA/mM | Glucose Response, nA/mM |
| 1(C/Si = 1) | 18,068 | 868 | 11,045 | 913 |
| 2(C/Si = 2) | 19,136 | 766 | 14,320 | 886 |
| 3(C/Si = 3.5) | 22,071 | 426 | 17,945 | 534 |

The data demonstrates a ten fold increase in peroxide response and a 2–3 fold increase in glucose response as compared to Example 2, as well as an improvement electrode stability. The data also shows that the ratio of platinized carbon to enzyme/silica can be varied while maintaining an acceptable glucose response.

EXAMPLE 4

Production of an Enzyme Electrode Using Glucose Oxidase and Thickening Agents

This example demonstrates the effects of a thickening agent on the enzyme electrode's response. It also shows the effect of the enzyme immobilization method on electrode stability and response linearity. The thickener (Acrysol SCT 200) produced coatings with higher peroxide responses and better repeatability from electrode to electrode. The reason for this is not known except to speculate that the thickener, which has hydrophobic and hydrophilic properties, may allow better permeation of solvent into the coating. Attachment of the GOD to the solid phase was accomplished in the following three ways: 1) covalent attachment of GOD to platinized carbon by carbodiimide coupling, 2) by ionic coupling to carbon and 3) by ionic coupling to silica, as described in Example 3.

Material

1. Platinized Vulcan XC 72 (carbon black) containing 10% platinum
2. GOD
3. MPBS
4. PBS/EDTA buffer (100 mm Na Phosphate, 100 mm NaCl, pH 6.0, containing 1 mM ethylene diamine tetra acetate and 0.1% Kathon CG as preservative)
5. MES buffer (50 mM Morpholino Ethane Sulfonate, pH 5.0)
6. EDAC (3 Ethyl 1(3-Dimethylaminopropyl) carbodiimide (available from Sigma Chemical Co., St. Louis, Mo.)
7. Magnifioc 591C (American Cyanamid Co., Wayne, N.J.)
8. Pyromellitic Dianhydride (1,2,4,5 Tetra carboxylate dianhydride, Aldrich Chemicals, Milwaukee, Wis.)

1. Covalent Attachment Method (EDC Method)

A solution containing 80 mg of EDC in 4 ml of water was added to a suspension of platinized carbon (1000 mg in 40 ml of MES buffer) to form a mixture. GOD (200 mg) was immediately added to the mixture and the mixture was mixed overnight (approximately 12 hours) at room temperature. After the overnight mixing, excess liquid was removed from the mixture. The carbon/GOD complexes were washed once with PBS/EDTA buffer before they were added to the various binding reagents.

2. PMA-GOD Carbon/Quat Attachment Method

GOD (200 mg) was dissolved in 20 ml of MPBS buffer to form a solution. One ml of a freshly prepared suspension of pyromellitic dianhydride (20 mg/ml in water) was added to the mixture to form a reaction mixture. The reaction mixture went from cloudy to clear in about 10 minutes at room temperature, indicating completion of the dianhydride acylation reaction. After the reaction was complete, the reaction mixture was combined with a suspension, which had been homogenized as above for 30 seconds, of platinized carbon (1000 mg), Magnifloc 591C (100 mg) and water (12.5 ml). The addition of the anionic GOD caused aggregation of the cationic carbon which was collected by centrifugation. The carbon/GOD complexes were then washed with PBS/EDTA buffer and centrifuged to remove the wash liquid.

3. PMA-GOD Silica/Quat

As previously mentioned the method used for this biopolymer/solid phase attachment procedure was the same as described in Example 3 except that the acetone drying step was deleted.

Resins
1. Acrylic Resin Mix A (no Thickener, 38.5% Non-Volatile Solids)

| Ingredient | % by weight |
|---|---|
| Joncryl 537 acrylic emulsion | 68.4 |
| Dibutyl Phthalate | 7.0 |
| Sodium Hydroxide (3% solution) | 8.7 |
| 2-Ethoxy ethanol | 20.6 |

2. Acrylic Resin Mix B (Contains Thickener, Acrysol)

| Ingredient | % by weight |
|---|---|
| Acrylic resin mix A | 76.9 |
| Acrysol SCT 200 (Rohm and Hass; Philadelphia, PA) | 23.1 |

Electrodes

The solid phase GOD preparations were combined with resin mixes in the amounts shown below (Table 5), then blended, dispensed and tested as in Example 3.

TABLE 5

| | Coating Formulations (mg of component) | | | |
|---|---|---|---|---|
| Component (Wet) | EDC | EDC/Acrysol | Carbon/Quat | Silica/Quat |
| GOD-EDC Carbon | 235 | 235 | | |
| GOD-Carbon/Quat | | | 505 | |
| GOD-Silica/Quat | | | | 390 |
| Acrylic Resin Mix A | 215 | | 224 | |
| Acrylic Resin Mix B | | 217 | | 433 |
| Water | 552 | 555 | 755 | 780 |
| Platinized Carbon | | | | 230 |

Using aqueous solutions of glucose (0.5 mM and 10 mM), the electrodes were tested shortly after they were manufactured and again after 11 days of wet storage at 45° C. Regression data are shown below in Table 6.

TABLE 6

| | Day 1 Data | | | Day 11 Data | | |
|---|---|---|---|---|---|---|
| Electrode | Slope, nA/mM | Y-int, nA | R | Slope, nA/mM | Y-int, nA | R |
| EDC-Carbon | 116 | 2 | 0.9997 | 72 | 8 | 0.9893 |
| EDC-Carb./Acrysol | 605 | 27 | 0.9980 | 168 | 20 | 0.9855 |
| Carbon/Quat | 886 | 196 | 0.9535 | 322 | 152 | 0.8183 |
| Silica/Quat/Acrysol | 885 | 27 | 0.9991 | 593 | 67 | 0.9876 |

The results shown in Table 6 show a particularly high glucose response when GOD is ionically bound to either carbon or silica. The silica bound enzyme also showed a good combination of signal, linearity and stability, even after heat stress.

EXAMPLE 5

Preparation of Cationic Silicas as Enzyme Binders

This example demonstrates that fumed and soluble silica can adsorb certain types of commercially available quaternary polymers to form materials which adsorb large quantities of anionic enzymes, as exemplified here by glucose oxidase or pyromellitic acid modified cholesterol oxidase.

Materials
1. GOD
2. Cholesterol Oxidase (Norcadia erythropolis, Boehringer Mannheim
   Biochemicals, Indianapolis, Ind.)
3. MPBS
4. PBS/EDTA
5. Snowtex UP, a 20% soluble colloidal silica solution
6. Fumed Silica (0.007 µ, Sigma Chemicals, St. Louis, Mo.)
7. Gafquat polymers (GAF Corporation, Wayne, N.J.)
8. Magnifloc polymers 491C–496 C series of polyacrylamide quaternary polymers (American Cyanamid Co., Wayne, N.J.)
9. Magnifloc polymers 567C–591C series of quaternary amine polymers (American Cyanamid Co., Wayne, N.J.)
10. Merquat -100 (Calgon Corp., Pittsburgh, Pa.)
11. Corcot P18 polyethyleneimine (Cordova Chemical Co., Mich.)
12. UCare polymers: Hydroxyethylcellulose se quaternary polymers at 1% w/v (Amerchol Corp., Edison, N.J.)

Procedure

Aqueous solutions (having concentrations ranging from 10–40 mg/ml) of the polymers shown in Table 7 were mixed with either soluble silica or fumed silica (approximately 0.5 to 2 mg polymer/mg silica) and the resulting precipitated silica suspensions were washed 3 times with water to remove excess polymer. The resulting silica/polymer complexes were tested for biopolymer binding affinity by adding approximately 1 mg of GOD per mg of silica. After a wash step, adsorption of the GOD to the complexes was determined visually. The presence of a yellow color associated with the complexes was considered indicative of a positive binding result. The binding results associated with the various polymers are shown in Table 7.

TABLE 7

| Polymer Name | Chemical Characteristics | GOD/Silica Binding Soluble | GOD/Silica Binding Fumed |
|---|---|---|---|
| 1. Gafquat 734 | Quaternized Vinylpyrrolidone | + | + |
| 2. Gafquat 755 | Quaternized Vinylpyrrolidone | − | +/− |
| 3. Gafquat 755N | Quaternized Vinylpyrrolidone | + | +/− |
| 4. Magnifloc 491C | High MW/Slight charge | − | − |
| 5. Magnifloc 492C | High MW/Moderate charge | − | − |
| 6. Magnifloc 494C | High MW/High charge | − | − |
| 7. Magnifloc 496C | High MW/Very high charge | − | − |
| 8. Magnifloc 567C | Low MW/High charge | − | + |
| 9. Magnifloc 572C | Very Low MW | − | − |
| 10. Magnifloc 577C | Moderate MW | − | +/− |
| 11. Magnifloc 579C | Highly charged | − | − |
| 12. Magnifloc 581C | High MW | − | + |
| 13. Magnifloc 591C | High MW | + | ++ |
| 14. Merquat 100 | High MW polyquaternium | + | ++ |
| 15. Corcat P18 | High MW Polyethyleneimine | + | ++ |
| 16. U-Care JR 125 | Highly charged | − | + |
| 17. U-Care JR 400 | Highly charged | − | + |
| 18. U-Care JR 30M | Highly charged | − | − |
| 19. U-Care LR 30M | Moderately charged | − | − |
| 20. U-Care LR 400 | Moderately charged | − | − |

Based on the results shown in Table 7, polymers 1, 8, 12, 13, 14, 15, 16, and 17 on fumed silica were tested for their binding affinity for pyromellitic acid (PMA) derivatized Cholesterol Oxidase (ChOD). The PMA/ChOD was prepared as described in Example 4 for glucose oxidase. However, in order to remove unreacted PMA, the procedure was supplemented with a desalting of the PMA/ChOD on a Sephadex® G-25 column (available from Pharmacia, Uppsala Sweden).

The PMA/ChOD (0.75 mg) thus produced was added to a solution of PBS containing 0.78 mg silica which had been bound with polymer The resulting solution was allowed to incubated at room temperature for 15 minutes with constant mixing. After the incubation, the solid phase was centrifuged and washed to remove unbound enzyme before it was resuspended in 1 ml of PBS/EDTA buffer. Appropriate dilutions of the finely divided solid phase enzyme were assayed for ChOD activity and compared to a soluble PMA/ChOD standard. Polymers 16 and 17 were not tested, since they did not visually appear to bind PMA ChOD. Enzyme activity was measured as a rate of color change in a peroxidase coupled colorimetric assay on an Abbott VISION® analyzer (a spectrophotometric centrifugal analyzer which allows the reaction mixture to be mixed between data measurements available from Abbott Laboratories, Abbott Park, Ill.). The results from this experiment are shown in Table 8.

Table 8 also shows the results from aliquots of the enzyme bound solid phase that were dried at room temperature for 3 days and reconstituted to measure the amount of activity retained.

TABLE 8

| Modifying Polymer | Bound PMA-ChOD, µg/ml | mg active PMA-ChOD bound/mg silica | After drying PMA ChOD, µg/ml | mg active PMA-ChOD retained/ mg silica |
|---|---|---|---|---|
| 1 | 146 | 0.19 | 90 | 0.11 |
| 8 | 260 | 0.33 | 201 | 0.26 |
| 12 | 352 | 0.45 | 187 | 0.24 |
| 13 | 310 | 0.40 | 192 | 0.25 |
| 14 | 401 | 0.51 | 124 | 0.16 |
| 15 | 234 | 0.30 | 115 | 0.15 |

The data shows that all of the treated silicas had a high binding capacity for the enzyme and, depending on the polymer used, there is a 2–3 fold variation in binding capacity and retention of activity after drying.

EXAMPLE 6

Production of an Enzyme Electrode Using Cholesterol Oxidase Covalently Bound to Fumed Silica This example demonstrates a covalent attachment method for cholesterol oxidase (ChOD) to aminated fumed silica. The immobilized ChOD was incorporated into a coating formulation and tested in an amperometric electrode format as demonstrated in Example 1.

Materials
1. Cholesterol Oxidase
2. MPBS (pH 7.5)
3. MES buffer (pH 6.0)
4. Fumed Silica
5. Aminopropyl Triethoxy Silane (A3648, Sigma Chemical Co., St. Louis, Mo.)
6. Magnifloc 591C quaternary amine polymer
7. 3 Ethyl 1-(3-Dimethylaminopropyl) carbodiimide (EDAC)
8. Trinitrobenzene Sulfonate (Sigma Chemical Co., St. Louis, Mo.)
9. Pyromellitic Dianhydride Procedure Fumed silica (1.0 gm) was vortexed with 10 ml of a 20% aqueous Aminopropyl Triethoxy Silane (ATS) solution and the pH was adjusted to 3.28 with 6N HCl to form a reaction mixture. The reaction mixture was heated to 70° C. in a water bath for 1 hour, washed twice with water, resuspended in MPBS buffer and stored as a wet slurry. The presence of amines was verified by the presence of an orange color when reacted with Trinitrobenzene Sulfonate.

A pyromellitic acid (PMA) derivative of ChOD was prepared as described in Example 5, desalted on a Sephadex® G-25 column and concentrated to 5.0 mg/ml using an Amicon® Centriprep 30 concentrator (available from Amicon® Corp., Beverly, Mass.). The enzyme was covalently coupled to the aminated silica as follows. Aminated fumed silica (wet equivalent of 250 mg dry silica) was washed with MES buffer and added to a solution of PMA ChOD (50 mg enzyme in 10 ml of MES buffer). EDAC (20 mg) was added to the solution which was then allowed to incubate overnight (approximately 12 hours) while being stirred. After the incubation, the silica/ChOD complexes thus formed were washed with MPBS buffer and stored in the buffer at 4° C. The activity of the complexes was 0.075 mg active enzyme/mg silica.

Electrodes were prepared as in Example 1 using the following resin formulation.

| Component | % by weight |
|---|---|
| Joncryl 537 acrylic emulsion | 36.1 |
| Dibutyl Phthalate | 39.3 |
| Ammonium Hydroxide (1.5N solution) | 1.0 |
| 2-Ethoxy ethanol | 23.6 |

The coating formulation used in this example was comprised of the following components.

| Component | Amount |
|---|---|
| PMA-ChOD/silica | 384 mg* |
| Platinized Carbon | 30 mg |
| Acrylic Resin Mix C | 130 mg |
| Distilled water | 456 mg |

*This weight is based on the wet weight of the complexes after being washed once with distilled water and centrifuged.

Four electrodes were prepared and tested (as above in Example 1) with a 500 µM cholesterol solution made up in a buffer comprising 100 mM sodium phosphate, 100 mM sodium chloride, 1 mM EDTA, 0.05% Kathon CG containing 0.75% Deoxycholate. The resulting amperometric response was 323+/−28 nA/500 µM.

EXAMPLE 7

Glutamate Oxidase Electrodes Using Defoamers and a Stabilizer

This example demonstrates the use of defoaming agents in a resin formulation designed to reduce the foaming which occurs during blending with the thickening agent Acrysol 275. With the formulation described below, defoaming of the coating formulation was reduced from overnight to less than two hours.

The formulation also includes a soluble disaccharide, trehalose (Sigma Chemical Co, St Louis, Mo.) in the coating solution. The presence of this material increased both the dry stability and the net signal of the electrodes as compared to coatings not containing the added stabilizer.

Materials and Procedure

Glutamate Oxidase (27% protein available from Yamasa Shoyu Co. Ltd.; Tokyo, Japan) was derivatized with pyromellitic anhydride and purified using the procedure described in Example 5. The PMA Glutamate Oxidase was then covalently coupled to amino derivatized fumed silica using the carbodiimide procedure described in Example 6 and stored wet. The wet, immobilized Glutamate Oxidase was 11% solids and contained 0.16 mg active enzyme/mg silica.

Platinized carbon (10% Platinum) was homogenized with MPBS buffer, washed 3 times with distilled water, centrifuged and stored wet. The wet platinized carbon contained 15% solids.

The resin formulation with defoamers contained the following:

| Acrylic Resin Mix D Components | % by weight |
|---|---|
| Joncryl 537 acrylic emulsion | 46.3 |
| Ammonium Hydroxide (1.5N) | 6.4 |
| Dibutyl phthalate* (Fluka Chemical, Buchs, Switzerland) | 5.1 |
| 2-Ethoxy ethanol* | 15.0 |
| Surfynol 104H (Air Products, Allentown, PA) | 1.9 |
| Surfynol 695 (Air Products, Allentown, PA) | 3.6 |
| Acrysol 275 (Rohm & Haas, Philadelphia, PA) | 21.8 |

*The dibutyl phthalate was dissolved in the 2-Ethoxy ethanol before being added to the acrylic emulsion Coating Solutions were prepared as described in Example 2, using the following formula:

| Component | mg |
|---|---|
| PMA Glutamate Oxidase-Silica (wet) | 206 |
| Platinized carbon (wet) | 151 |
| Acrylic Resin Mix D | 140 |
| Trehalose (0.085M in water) | 502 |

Electrodes were prepared as in Example 1 using 0.8 µl of the coating solution and curing the electrodes in a desiccated room temperature environment for 1 week. Electrodes were then tested in continuous wet use for 7 days at 37° C. Every 2 hours, glutamate response in buffer and in diluted bovine plasma (1 part plasma+3 parts MPBS buffer, pH 6.5) was measured as described in Example 1. The linearity of the glutamate response was measured before and after this stability study and is shown below in Table 10. The electrode retained over 40% of its initial response after 7 days of 37° C. use while maintaining a linear response to glutamate.

TABLE 9

| Glutamate (mM) | Net nA (Pre-Stability) | Net nA (Post-Stability) |
|---|---|---|
| 0 | 0 | 0 |
| 0.025 | 146 | 51 |
| 0.050 | 255 | 97 |
| 0.100 | 480 | 182 |
| 0.150 | 654 | 289 |
| 0.200 | 841 | 354 |
| 0.250 | 1089 | 438 |
| Slope | 4.19 | 1.75 |
| Int | 31.2 | 17.3 |
| R^2 | 0.997 | 0.997 |

The electrodes were allowed to dry and were heat stressed by storing them at 37° C. for 5 weeks. After the heat stress the electrodes were tested and the electrode response (average of 4 electrode spots) was 1033 nA/250 µM glutamate, a loss of only 5% compared with the 1089 nA before heat stress.

EXAMPLE 8

Production of an Electrode Using Metalloporphyrin as a Hydrogen Peroxide Catalyst This example demonstrates the use of a metalloporphyrin as a hydrogen peroxide oxidation catalyst. Instead of using platinized carbon (10% Platinum) in the coating solution, unplatinized activated carbon treated with a metalloporphyrin was used. Additionally, bovine serum albumin (BSA) covalently attached to fumed silica was incorporated into the coating instead of an enzyme bound to a solid phase. Electrodes were prepared according to the procedure in Example 7.

Materials
1. Vulcan XC 72R (carbon black) with no platinum (Cabot Industries, Waltham, Mass.)
2. Protoporphyrin IX dimethyl ester (Sigma Chemical Company, St. Louis Mo.)
3. Cobalt chloride (Sigma Chemical Company, St. Louis, Mo.)
4. Bovine Serum Albumin (Sigma Chemical Company, St. Louis, Mo.)
5. Fumed Silica
6. Aminopropyl Triethoxy Silane
7. 3 Ethyl 1-(3-Dimethylaminopropyl) carbodiimide
8. MES buffer (pH 5.5)
9. MPBS buffer (pH 7.5)

Procedure;

25.0 ml of N,N-dimethyl formamide (DMF) was brought to reflux in a 100 ml round bottom flask before 200 mg of protoporphyrin IX dimethyl ester was added to the flask. The mixture was stirred with a stir bar until the porphyrin was dissolved. 210 mg of cobalt chloride was then added to the flask and the mixture was refluxed for 10 minutes before the flask was removed from the heat source. The excess solvent was evaporated from the the reaction mixture, the reaction mixture was transferred to a 250 mL Erlenmeyer flask, and 125 ml of ice water was added. The flask was then placed in a ice bath for approximately 20 minutes and the resulting solid cobalt protoporphyrin (CoPP) was recovered by filtration and air-dried overnight. A solution of CoPP (15.4 mg in 0.75 ml chloroform) was added to 500 mg of homogenized, MPBS washed carbon. The reaction mixture was stirred for 30 minutes before the carbon mixture was centrifuged and the supernatent discarded. The carbon was washed 3 times with distilled water.

Fumed silica was aminated with aminopropyl triethoxy silane as in Example 6 and the BSA was covalently coupled to the aminated silica as follows. Aminated fumed silica (wet equivalent of 250 mg dry silica) was washed with MES buffer and added to a solution of BSA (51.0 mg in 10.0 ml MES buffer). EDAC (20 mg) was added to the solution which was then allowed to stir overnight. The silica/BSA complex was then washed with MPBS buffer.

A Coating Solution was prepared as described in Example 7, using the following formula:

| Component | mg |
| --- | --- |
| BSA-Silica (wet) | 103 |
| Cobalt protoporphyrin (CoPP) modified carbon (wet) | 76 |
| Acrylic Resin Mix D | 70 |
| Trehalose (0.085M in water) | 251 |

Electrodes were prepared, as in Example 3, using 0.8 μL of the coating solution. For comparison, a coating solution containing 10% platinized carbon, instead of the CoPP modified carbon, was prepared using the above components and used to prepare electrodes. The platinized carbon was incubated with chloroform in the same manner as the CoPP modified carbon. Two electrodes of each type were tested for electrochemical response with a 100 mM hydrogen peroxide solution at various applied potentials. The data shown in Table 11 demonstrates that cobalt protoporphyrin on carbon catalyzes hydrogen peroxide oxidation in a manner similar to platinum on carbon.

TABLE 10

| Applied Potential (mV) | CoPP Modified Carbon Electrode Response to $H_2O_2$ (nA) | Platinized Carbon Electrode Response to $H_2O_2$ (nA) |
| --- | --- | --- |
| 350 | 1039 | 1487 |
| 250 | 416 | 1012 |
| 200 | 152 | 611 |
| 150 | 18 | 179 |

What is claimed is:

1. An immobilization medium comprising:
   a. a bioreagent immobilized to a solid phase, wherein said solid phase is comprised of particles with a polymer absorbed thereon, wherein said adsorbed polymer is selected from the group consisting of quaternary ammonium polymers, tertiary amino polymers, secondary amino polymers, and primary amino polymers; and
   b. a latex resin, wherein said immobilized bioreagent is evenly dispersed in said latex resin; wherein said immobilization medium is a substantially homogeneous dispensable mixture.

2. The medium of claim 1 wherein said bioreagent is selected from the group consisting of analytes and analyte analogs.

3. The medium of claim 1 wherein said bioreagent is an enzyme.

4. The medium of claim 1 wherein said bioreagent is an antibody or an antibody fragment.

5. The medium of claim 1 wherein said bioreagent is a nucleic acid.

6. The medium of claim 1, wherein said particles comprise a material selected from the group consisting of inorganics, organics, carbohydrates and combination of two or more inorganics, organics, and carbohydrates.

7. The medium of claim 6 wherein said particle are selected from the group consisting of silica particles, agarose particles, cellulose particles, derivatized cellulose particles, carbon particles, platinized carbon particles, graphite particles, platinized graphite particles, aluminum oxide particles, aluminosilicate particles, titanium dioxide particles, platinum group metal oxide particles, metalloporphyrin carbon particles, metalloporphyrin graphite particles, and combinations of two or more silica particles, agarose particles, cellulose particles, derivatized cellulose particles, carbon particles, platinized carbon particles, graphite particles, platinized graphite particles, aluminum oxide particles, aluminosilicate particles, titanium dioxide particles, platinum group metal oxide particles metalloporphyrin carbon particles, and metalloporphyrin graphite particles.

8. The medium of claim 7 wherein said particles are finely divided.

9. The medium of claim 6, wherein said organics further comprise synthetic organics.

10. The medium of claim 1 wherein said latex resin is selected from the group consisting of an acrylic latex, a styrene acyrlic latex, a vinyl acetate latex, a polyurethane latex and combinations of two or more of an acrylic latex, a styrene acyrlic latex, a vinyl acetate latex and a polyurethane latex.

11. The medium of claim 1 further comprising means for modifying the chemical and physical properties of the immobilization medium.

12. The medium of claim 11 wherein said modifying means are selected from the group consisting of plasticizers, thickeners, film forming agents, stabilizers, dispersing agents, defoaming agents, electrochemically active agents and combinations of two or more plasticizers, thickeners, film forming agents, stabilizers, dispersing agents, defoaming agents, and electrochemically active agents.

13. The medium of claim 1, wherein said bioreagent is selected from the group consisting of detectable moieties and specific binding members.

14. The medium of claim 1, wherein said bioreagent is covalently immobilized to said solid phase.

15. The medium of claim 1, wherein said bioreagent is ionically immobilized to said solid phase.

* * * * *

UNITED STATES PATENT AND TRADEMARK OFFICE
CERTIFICATE OF CORRECTION

PATENT NO.   :  5,643,721
DATED        :  July 1, 1997
INVENTOR(S)  :  Spring et al.

It is certified that error appears in the above-indentified patent and that said Letters Patent is hereby corrected as shown below:

Column 26, line 26, change "quaternary" to --quarternary--.

Signed and Sealed this

Twenty-eighth Day of October, 1997

Attest:

BRUCE LEHMAN

*Attesting Officer*     *Commissioner of Patents and Trademarks*